United States Patent [19]

Gibson et al.

[11] Patent Number: 5,451,511
[45] Date of Patent: Sep. 19, 1995

[54] PROCESS FOR THE PREPARATION OF ANTIPARASITIC AGENTS

[75] Inventors: Stephen P. Gibson; Alexander C. Goudie; Kelvin S. Holdom; John D. Bu'Lock, all of New York, N.Y.

[73] Assignee: Pfizer Inc., New York, N.Y.

[21] Appl. No.: 28,459

[22] Filed: Mar. 9, 1993

Related U.S. Application Data

[60] Continuation of Ser. No. 786,862, Nov. 1, 1991, abandoned, which is a division of Ser. No. 142,888, Jan. 11, 1988, Pat. No. 5,089,480, which is a continuation-in-part of Ser. No. 886,867, Jul. 16, 1986, abandoned.

[30] Foreign Application Priority Data

| Jul. 27, 1985 | [GB] | United Kingdom | 8518999 |
| Aug. 9, 1985 | [GB] | United Kingdom | 8520069 |
| Apr. 24, 1986 | [GB] | United Kingdom | 8610063 |
| May 2, 1986 | [GB] | United Kingdom | 8610862 |

[51] Int. Cl.$^6$ ............................................. C12P 19/62
[52] U.S. Cl. ..................................... 435/76; 435/886; 536/7.1
[58] Field of Search ............... 435/76, 886; 536/7.1

[56] References Cited

U.S. PATENT DOCUMENTS

| 4,134,973 | 1/1979 | Fisher et al. | 424/180 |
| 4,156,720 | 5/1979 | Fisher et al. | 424/180 |

(List continued on next page.)

FOREIGN PATENT DOCUMENTS

| 1689 | 5/1979 | European Pat. Off. |
| 2615 | 6/1979 | European Pat. Off. |

(List continued on next page.)

OTHER PUBLICATIONS

Fisher & Mrozik, Macrolide Antibiotics, Academic Press (1984), Chp. 14.

(List continued on next page.)

*Primary Examiner*—Douglas W. Robinson
*Assistant Examiner*—Elli Peselev
*Attorney, Agent, or Firm*—Peter C. Richardson; Gregg C. Benson

[57] ABSTRACT

The invention provides novel compounds having the formula:

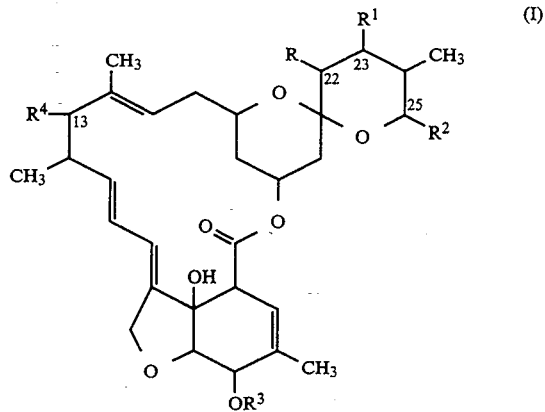

wherein R when taken individually is H; $R^1$ when taken individually is H or OH; R and $R^1$ when taken together represent a double bond;

$R^2$ is an alpha-branched $C_3$–$C_8$ alkyl, alkenyl, alkynyl, alkoxyalkyl or alkylthioalkyl group; a $C_3$–$C_8$ cycloalkyl, $C_5$–$C_8$ cycloalkenyl or $C_5$–$C_8$ cycloalkylalkyl group, any of which may be substituted by methylene or one or more $C_1$–$C_4$ alkyl groups or halo atoms; or a 3 to 6 membered oxygen or sulphur containing heterocyclic ring which may be substituted by one or more $C_1$–$C_4$ alkyl groups or halo atoms;

$R^3$ is hydrogen or methyl;

$R^4$ is H or 4'-(alpha-L-oleandrosyl)-alpha-L-oleandrosyloxy with the proviso that when $R^2$ is alkyl it is not isopropyl or sec-butyl; when $R^4$ is H, each of R and $R^1$ is H, and $R^2$ is not methyl or ethyl; and when $R^4$ is H, R is H, $R^1$ is OH, and $R^2$ is not 2-buten-2-yl, 2-penten-2-yl or 4-methyl-2-penten-2-yl.

The compounds are broad spectrum antiparasitic agents having utility as anthelmintics, ectoparasiticides, insecticides and acaricides. The invention also provides a process for producing the novel avermectin and milbemycin derivatives by adding a carboxylic acid or derivative thereof to a fermentation of an avermectin or milbemycin producing organism.

4 Claims, No Drawings

U.S. PATENT DOCUMENTS

| | | | |
|---|---|---|---|
| 4,199,569 | 4/1980 | Chabla et al. | 424/180 |
| 4,200,581 | 4/1980 | Fisher et al. | 424/180 |
| 4,285,963 | 8/1981 | Arison et al. | 424/279 |
| 4,310,519 | 1/1982 | Albers-Schonberg et al. | 424/181 |
| 4,328,335 | 5/1982 | Mrozik | 536/7.1 |
| 4,333,925 | 6/1982 | Buhs et al. | 424/181 |
| 4,378,353 | 3/1983 | Goegelman et al. | 424/181 |
| 4,423,209 | 12/1983 | Mrozik | 536/7.1 |
| 4,429,042 | 1/1984 | Albers-Schonberg et al. | 435/119 |
| 4,831,016 | 5/1989 | Mrozik | 514/30 |
| 4,980,370 | 12/1990 | Dutton et al. | 536/7.1 |

FOREIGN PATENT DOCUMENTS

| | | |
|---|---|---|
| 215654 | 3/1987 | European Pat. Off. . |
| 235085 | 9/1987 | European Pat. Off. . |
| 241147 | 10/1987 | European Pat. Off. . |
| 58-78594 | 5/1983 | Japan . |
| 2166436 | 5/1986 | United Kingdom . |
| 2167751 | 6/1986 | United Kingdom . |
| 2170499 | 8/1986 | United Kingdom . |
| 2176182 | 12/1986 | United Kingdom . |

OTHER PUBLICATIONS

Schulman, et al., J. Antibiot. 38(11): 1494–1498 (1985).
Schulman et al., Fed. Proc. 44: 931 (1985).
Chen et al., Abstr. Pap. Am. Chem. Soc., 1983, 186 Meet. MBTD 28.
Ruby et al., 6th Intnl. Symp. on "Biology of Actinomycetes," Debrecen, Hungary, Aug. 26–30 (1985), pp. 279–280.
Schulman et al., Antimicrobial Agents and Chemotherapy 29: 620–624 (1986).
Schulman et al., Antimicrobial Agents and Chemotherapy 31: 744–747 (1987).
Derwent Abstract, Accession No. 84–01600.
Cane, D. E. et al., J. Am. Chem. Soc. 105: 4110–4112 (1983).
Kaneda, T., Can. J. Microbiol. 12: 501–514 (1966).
Dreher, R. et al., J. Bacteriol. 127: 1136–1140 (1976).
Kaneda, T., Biochem. Biophys. Res. Commun. 99: 1226–1229 (1981).
Oshima, M. et al., J. Biol. Chem. 250: 6963–6968 (1975).
Poralla, K. et al., FEMS Microbiol. Lett. 16: 303–306 (1983).
DeRosa, M. et al., Phytochemistry 13: 905–910 (1974).
Claridge, C. A., Basic Life Sciences 25: 231–269 (1983).
Sebek, O. K., Biotechnology, Chapter 7, "Antibiotics", Kieslick (Ed.) 1984, pp. 239–276.
Ballio et al., Amn. Inst. Pasteur 114:121–137 (1968).
Behrens, O. K., J. Biol. Chem. 175:771–792 (1948).
Behrens, O. K., J. Biol. Chem. 175:793–809 (1948).

PROCESS FOR THE PREPARATION OF ANTIPARASITIC AGENTS

CROSS-REFERENCE TO RELATED APPLICATION

This application is a continuation of application Ser. No. 07/786,862, filed Nov. 1, 1991, now abandoned, which is a divisional application of application Ser. No. 07/142,888, filed Jan. 11, 1988, now U.S. Pat. No. 5,089,480, which is a continuation-in-part of application Ser. No. 886,867, filed Jul. 16, 1986, now abandoned.

BACKGROUND OF THE INVENTION

1. Field of the Invention

This invention relates to antiparasitic agents and in particular to compounds related to the avermectins and milbemycins but having a novel substituent group at the 25-position and to a process for their preparation.

2. Description of the Prior Art

The avermectins are a group of broad spectrum antiparasitic agents referred to previously as the C-076 compounds. They are produced by fermenting a strain of the microorganism Streptomyces avermitilis ATCC 31267, 31271 or 31272 under aerobic conditions an aqueous nutrient medium containing inorganic salts and assimilable sources of carbon and nitrogen. The morphological and cultural properties of the strains ATCC 31267, 31271 and 31272 are described in detail in British Patent Specification No. 1573955 which also describes the isolation and the chemical structure of the eight individual components which make up the C-076 complex. The milbemycins are structurally related macrolide antibiotics lacking the sugar residues at the 13-position. They are produced by fermentation, for example as described in British Patent Specification No. 1390336 and European Patent Application Publication No. 0170006.

SUMMARY OF THE INVENTION

We have now discovered that by adding certain specified carboxylic acids, or derivatives thereof, to the fermentation of an avermectin producing organism it is possible to obtain novel compounds, related to the avermectins but having an unnatural substituent group at the 25-position in place of the isopropyl or sec-butyl group which is normally present. The novel compounds are highly active antiparasitic agents having particular utility as anthelmintics, ectoparasiticides, insecticides and acaricides.

Thus, according to one aspect of the invention there is provided a process for producing a novel avermectin derivative having an unnatural substituent group at the 25-position which comprises adding a carboxylic acid, or a salt, ester or amide thereof or oxidative precursor therefor, to a fermentation of an avermectin producing organism, and isolating the novel avermectin derivative.

Conventional chemical transformation reactions can be used to prepare further derivatives from these compounds. Thus, according to a further aspect of the invention there are provided compounds having the formula:

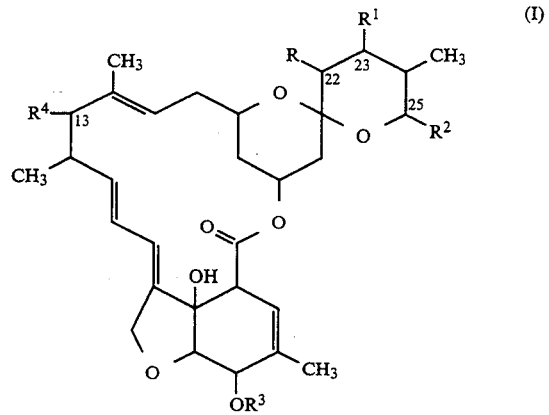

wherein R when taken individually is H; when taken $R^1$ when taken individually is H or OH; R and $R^1$ when taken together represent a double bond;

$R^2$ is an alpha-branched $C_3$-$C_8$ alkyl, alkenyl, alkynyl, alkoxyalkyl or alkylthioalkyl group; a $C_5$-$C_8$ cycloalkylalkyl group wherein the alkyl group is an alpha-branched $C_2$-$C_5$ alkyl group; a $C_3$-$C_8$ cycloalkyl or $C_5$-$C_8$ cycloalkenyl group, either of which may be substituted by methylene or one or more $C_1$-$C_4$ alkyl groups or halo atoms; or a 3 to 6 membered oxygen or sulphur containing heterocyclic ring which may be saturated, or fully or partially unsaturated and which may be substituted by one or more $C_1$-$C_4$ alkyl groups or halo atoms;

$R^3$ is hydrogen or methyl;

$R^4$ is H or a 4'-(alpha-L-oleandrosyl)-alpha-L-oleandrosyloxy group of the formula:

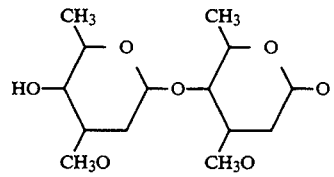

with the proviso that when $R^2$ is alkyl it is not isopropyl or sec-butyl; when $R^4$ is H, each of R and $R^1$ is H, and $R^2$ is not methyl or ethyl; and when $R^4$ is H, R is H, $R^1$ is OH, and $R^2$ is not 2-buten-2-yl, 2-penten-2-yl or 4-methyl-2-penten-2-yl.

In the above definition, alkyl groups containing 3 or more carbon atoms may be straight or branched chain. Halo means fluoro, chloro, bromo or iodo. Alpha-branched means that the carbon atom attached to the 25-ring position is a secondary carbon atom linked to two further carbon atoms. When $R^2$ is alkyl of 5 or more carbon atoms, the remainder of the alkyl chain may be straight or branched chain.

Preferred compounds of the formula I are those wherein $R^4$ is 4'-(alpha-L-oleandrosyl)-alpha-L-oleandrosyloxy. Also preferred are compounds of the formula I wherein $R^2$ is a $C_5$ or $C_6$ cycloalkyl or cycloalkenyl group which may be substituted by one or more $C_1C_4$ alkyl groups, cyclopentyl and cyclohexyl being particularly preferred. In another group of preferred compounds $R^2$ is cyclobutyl. In a further group of preferred compounds $R^2$ is a 5 or 6 membered oxygen or sulphur containing heterocyclic ring, particularly a 3-thienyl or 3-furyl ring, which may be substituted by one or more $C_1$–$C_4$ alkyl groups or halogen atoms. In a yet further group of preferred compounds, $R^2$ is a $C_3$–$C_8$ alkylthioalkyl group, particularly a 1-methylthioethyl group.

DETAILED DESCRIPTION OF THE INVENTION

In accordance with the invention the compounds of formula I wherein R is H and $R^1$ is OH or wherein R and $R^1$ taken together represent a double bond, and $R^4$ is 4'-(alpha-L-oleandrosyl)-alpha-L-oleandrosyloxy are prepared by fermenting an avermectin producing organism, such as a strain of the organism *Streptomyces avermitilis* ATCC 31267, 31271 or 31272, in the presence of the appropriate carboxylic acid of the formula $R^2CO_2H$, wherein $R^2$ is as previously defined, or a salt, ester, or amide thereof or oxidative precursor therefor. The acid is added to the fermentation either at the time of inoculation or at intervals during the fermentation. Production of the compounds of formula (I) may be monitored by removing samples from the fermentation, extracting with an organic solvent and following the appearance of the compound of formula (I) by chromatography, for example using high pressure liquid chromatography. Incubation is continued until the yield of the compound of formula (I) has been maximised, generally for a period of from 4 to 6 days.

A preferred level of each addition of the carboxylic acid or derivative thereof is between 0.05 and 1.0 grams per liter. The best yields of the compounds of formula (I) are obtained by gradually adding the acid to the fermentation, for example by daily additions of the acid or derivative thereof over a period of several days. The acid is preferably added as a salt, such as the sodium or ammonium salt, but may be added as an ester, such as the methyl or ethyl ester or as an amide. Alternative substrates which may be used in the fermentation are derivatives which are oxidative precursors for the carboxylic acids; thus, for example suitable substrates would be aminoacids of the formula $R^2CH(NH_2)CO_2H$, glyoxylic acids of the formula $R^2COCO_2H$, methylamine derivatives of the formula $R^2CH_2NH_2$, substituted lower alkanoic acids of the formula $R^2(CH_2)_nCO_2H$ wherein n is 2, 4 or 6, methanol derivatives of the formula $R^2CH_2OH$ or aldehydes of the formula $R^2CHO$, wherein $R^2$ is as previously defined. The media used for the fermentation may be a conventional complex media containing assimilable sources of carbon, nitrogen and other trace elements. However we have found that for better results a strain of the organism derived from *Streptomyces avermitilis* ATCC 31271 which gives improved yields of a compound of formula I when cultured in a semi-defined medium may be used and this has the advantage that crude solvent extracts contain significantly less unwanted material which greatly simplifies the subsequent isolation and purification stages. Such a strain has been deposited with the National Collection of Industrial Bacteria (NCIB) on 19th Jul. 1985 under the accession number NCIB 12121. The morphological and cultural characteristics of this strain are otherwise generally as described in British Patent specification No. 1573955 for strain ATCC 31267.

After fermentation for a period of several days at a temperature preferably in the range of from 24° to 33° C., the fermentation broth is centrifuged or filtered and the mycelial cake is extracted with acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product containing the compounds of formula (I) is further purified as necessary by chromatography, for example using preparative reverse phase, high pressure liquid chromatography.

The product is generally obtained as a mixture of the compounds of formula (I) wherein $R^4$ is 4'-(alpha-L-oleandrosyl)-alpha-L-oleandrosyloxy, R is H, $R^1$ is OH or R and $R^1$ taken together represent a double bond and wherein $R^3$ is H or $CH_3$; however the proportions can vary depending on the particular carboxylic acid employed and the conditions used.

We have found that a broad range of carboxylic acids as defined by $R^2CO_2H$ may be added to the fermentation to yield avermectins having a novel substituent group at the 25-position. Examples of particular acids which may be employed include the following:

2-methylvaleric acid
2-methylpent-4-enoic acid
2-methylthiopropionic acid
2-cyclopropyl propionic acid
cyclobutane carboxylic acid
cyclopentane carboxylic acid
cyclohexane carboxylic acid
cycloheptane carboxylic acid
2-methylcyclopropane carboxylic acid
3-cyclohexene-1-carboxylic acid
and thiophene-3-carboxylic acid In one particular and preferred aspect of the invention, the fermentation is performed in the presence of cyclopentane carboxylic acid sodium salt to yield predominantly the compound of formula (I) wherein R is H, $R^1$ is OH, $R^2$ is cyclopentyl, $R^3$ is $CH_3$ and $R^4$ is 4'-(alpha-L-oleandrosyl)-alpha-L-oleandrosyloxy.

In another preferred aspect of the invention, the fermentation is performed in the presence of thiophene-3-carboxylic acid sodium salt to yield predominantly the compound of (I) where R is H, $R^1$ is OH, $R^2$ is thien-3-yl, $R^3$ is $CH_3$ and $R^4$ is 4'-(alpha-L-oleandrosyl)-alpha-L-oleandrosyloxy.

In a further preferred aspect of the invention the fermentation is performed in the presence of 2-methylthiopropionic acid sodium salt to yield predominantly the compound of formula (I) wherein R is H, $R^1$ is OH, $R^2$ is 1-methylthioethyl, $R^3$ is $CH_3$ and $R^4$ is 4'-(alpha-L-oleandrosyl)-alpha-L-oleandrosyloxy.

Compounds of the formula (I) wherein the $C_{22-23}$ double bond is present may alternatively be prepared from the corresponding compound of formula (I) wherein R is H and $R^1$ is OH by a dehydration reaction. The reaction is performed by first selectively protecting the hydroxyl groups at the 5 and 4" positions, e.g. as the t-butyldimethylsilyloxy acetyl derivative, then reacting with a substituted thiocarbonyl halide, such as (4-methylphenoxy)thiocarbonyl chloride, followed by heating in a high boiling point solvent, e.g. trichlorobenzene, to effect the dehydration. The product is finally deprotected to give the unsaturated compound. These steps together with appropriate reagents and reaction conditions are described in U.S. Pat. No. 4,328,335.

The compounds of formula I wherein $R^3$ is H may also be prepared from the corresponding compounds wherein $R^3$ is $CH_3$ by demethylation. This reaction is achieved by treating the 5-methoxy compound, or a suitably protected derivative thereof, with mercuric acetate and hydrolysing the resulting 3-acetoxy enol ether with dilute acid to give the 5-keto compound. This is then reduced using, for example, sodium borohydride to yield the 5-hydroxy derivative. Appropriate reagents and reaction conditions for these steps are described in U.S. Pat. No. 4,423,209.

The compounds of formula I wherein each of R and $R^1$ is H can be prepared from the corresponding compound wherein the double bond is present at $C_{22}$–$C_{23}$ by selective catalytic hydrogenation using an appropriate catalyst. For example the reduction may be achieved using tris(triphenylphosphine)rhodium (I) chloride as described in European patent application publication No. 0001689.

The compounds of formula (I) wherein $R^4$ is H are prepared from the corresponding compounds wherein $R^4$ is 4'-(alpha-L-oleandrosyl)-alpha-L-oleandrosyloxy by removing the 4'-(alpha-L-oleandrosyl)-alpha-L-oleandrose group by mild hydrolysis with an acid in an aqueous organic solvent to yield the aglycone having a hydroxy group at the 13-position; this is then halogenated, for example by reaction with a benzene sulphonyl halide, to yield the 13-deoxy-13-halo derivative which is finally selectively reduced, for example using tributyltin hydride. In order to avoid unwanted side reactions it is desirable to protect any other hydroxy groups which may be present, for example using a tert-butyldimethylsilyl group. This is then readily removed after the halogenation or reduction step by treatment with methanol containing a trace of acid. All these steps together with appropriate reagents and reaction conditions for their performance are described in European patent application publication No. 0002615.

Compounds of the formula (I) wherein each of R and $R^4$ is H and $R^1$ is either H or OH, may also be prepared by adding the appropriate carboxylic acid, or a salt, ester or amide thereof or oxidative precursor therefor, to a fermentation of a milbemycin producing organism, and isolating the desired milbemycin derivative having an unnatural substituent group at the 25-position. Examples of milbemycin producing organisms include for instance *Streptomyces hygroscopicus* strain NRRL 5739 as described in British Patent Specification No. 1390336, *Streptomyces cyaneogriseus* subsp. *noncyanogenus* NRRL 15773 as described in European patent application publication No. 0170006 and *Streptomyces thermoarchaenis* NCIB 12015 as described in GB 2166436A.

The compounds of the invention are highly active antiparasitic agents having particular utility as anthelmintics, ectoparasiticides, insecticides and acaricides.

Thus the compounds are effective in treating and preventing a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites such as Ancylostoma, Necator, Ascaris, Strongyloides, Trichinella, Capillaria, Trichuris, Enterobius and parasites which are found in the blood or other tissues and organs such as filiarial worms and the extra intestinal stages of Strongyloides and Trichinella.

The compounds are also of value in treating and preventing ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (I) are administered as a formulation appropriate to the specific use envisaged and to the particular species of host animal being treated and the parasite or insect involved. For use as an anthelmintic the compounds may be administered orally in the form of a capsule, bolus, tablet or preferably a liquid drench, or alternatively, they may be administered by injection or as an implant. Such formulations are prepared in a conventional manner in accordance with standard veterinary practice. Thus, capsules, boluses or tablets may be prepared by mixing the active ingredient with a suitable finely divided diluent or carrier additionally containing a disintegrating agent and/or binder such as starch, lactose, talc, magnesium stearate, etc. A drench formulation may be prepared by dispersing the active ingredient in an aqueous solution together with dispersing or wetting agents etc. and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral administration a dose of from about 0,001 to 10 mg per Kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, emulsions and the like in accordance with standard agricultural practice.

The invention is illustrated by the following Examples in which Examples 1 to 21 are Examples of the preparation of compounds of the formula (I), Example 22 is an example of a drench formulation and Examples 23 and 24 illustrate the antiparasitic and insecticidal activity of the compounds.

EXAMPLE 1

25-Cyclopentyl-avermectin A2

A suspension of a slope culture of *S. avermitilis* NCIB 12121 was inoculated into 600 ml of a medium containing lactose (12.0 g), distillers solubles (8.0 g) and yeast extract (3.0 g), contained in a 3 liter flask, and incubated at 28° C. for 3 days. The inoculum was used to inoculate 16 liters of a medium containing soluble starch (640 g), ammonium sulphate (32 g), dipotassium hydrogen phosphate (16 g), sodium chloride (16 g), magnesium sulphate 7H$_2$O (16 g), calcium carbonate (32 g), soluble yeast extract (6.4 g), ferrous sulphate 7H$_2$O (0.016 g), zinc sulphate 7H$_2$O (0.016 g) and manganese chloride 4H$_2$O (0.016 g), contained in a 20 liter fermenter. The fermentation was incubated at 28° C., with agitation at 250 r.p.m. and aerated at 15 liters per minute. Cyclopentane carboxylic acid sodium salt (1.6 g) was added after 24 hours and again after 48 and 72 hours incubation and the fermentation was continued for 120 hours. After this time the mycelium was removed by filtration and extracted with acetone: 1N-hydrochloric acid (100:1; 3×7 liters). The extract was concentrated to approximately 2 liters under reduced pressure and extracted with methylene chloride (2×5 liters). The methylene chloride extract was concentrated to dryness to give the crude product as a mobile oil which was dissolved in diethyl ether and added to a column of silica gel (1 kg). The column was eluted with diethyl ether collecting 100 ml fractions. Fractions 20–40 were combined and the solvent evaporated to yield partially purified material. The product was dissolved in a mixture of methanol and water (4:1) and chromatographed on a C18 Micro-Bondapack column (50 mm×50 cm) in a Waters Prep 500 high pressure liquid chromatograph using the same solvent at a flow rate of 100 ml per minute. Fractions 35 to 50 containing the desired product were combined and rechromatographed on a C18 Zorbax ODS (Trademark, Dupont) column (21 mm×25 cm) eluting with a mixture of methanol and water (4:1) at a flow rate of 9 ml per minute. The relevant fractions were combined and the solvent evaporated to yield the compound of formula (I) wherein R is H, R$^1$ is OH, R$^2$ is cyclopentyl, R$^3$ is CH$_3$ and R$^4$ is 4'-(alpha-L-oleandrosyl)-alpha-L-oleandrosyloxy as a white powder, m.p. 150.5°–151° C. The structure of the product was confirmed by mass spectrometry and by C13 nuclear magnetic resonance spectroscopy as follows:

Fast atom bombardment mass spectrometry was performed on a VG Model 7070E mass spectrometer using a sample matrix of triethylene glycol with solid sodium chloride. (M+Na)$_+$ observed at m/e 939 (theoretical 939).

Electron impact mass spectrometry was performed using a VG Model 7070F mass spectrometer. The m/e values for the principal fragments were: 335, 317, 275, 257, 251, 233, 205, 181, 179, 145, 127, 113, 111, 95 and 87.

The 13C nuclear magnetic resonance spectral data were obtained on a Brucker Model WM-250 spectrometer with a sample concentration of 20 mg/ml in deuterochloroform. The chemical shifts in parts per million relative to tetramethylsilane were: 14.1, 15.3, 17.8, 18.5, 19.9, 20.3, 24.6 25.9, 26.2, 29.3, 34.4 (2C), 34.7, 36.7, 37.8, 39.8, 40.5, 41.0, 41.3, 45.8, 56.4, 56.6, 57.8, 67.4, 67.6, 68.0, 68.3, 68.7, 69.9, 70.5, 76.0, 77.6 (2C), 78.3, 79.5, 80.7 (2C), 81.8, 94.9, 98.7, 99.8, 117.7, 118.5, 119.8, 125.0,135. 8,136.3, 137.8, 140.1 and 173.8.

EXAMPLE 2

A suspension of a slope culture of *S. avermitilis* ATCC 31271 was inoculated into 50 ml of a medium containing lactose (1.0 g), distillers solubles (0.75 g) and yeast extract (0.25 g), contained in a 350 ml flask, and incubated at 28° C. for 3 days. This inoculum 4 ml) was used to inoculate each of 50 flasks containing 50 ml of medium containing corn starch (2.0 g), soya flour (0.35 g) and yeast extract (0.25 g) contained in a 350 ml flask, and the flasks were incubated at 28° C.

After 24 hours, cyclopentane carboxylic acid sodium salt (5 mg) was added to each flask and incubation was continued for a further 5 days. After this time the contents of the flasks were bulked and the mycelium separated by centrifugation. The mycelium was extracted with acetone: 1N-hydrochloric acid (100:1) and the acetone extract concentrated to dryness. The extract was analysed by high pressure liquid chromatography and was shown to contain a product identical with the product of Example 1.

EXAMPLE 3

An inoculum was prepared as described in Example 1 and used to inoculate 50 ml of the medium as used in Example 1, contained in 350 ml flasks. After incubation for 24 hours, 2-aminocyclopentyl acetic acid (cyclopentylglycine) (5 mg) was added and the fermentation was continued for a further 5 days. The product was recovered by extraction of the mycelium with acetone and methylene chloride. The extract was analyzed by HPLC which indicated that the product contained a compound identical to the product of Example 1.

EXAMPLE 4

The conditions of Example 3 were followed except that cyclopentyl methanol was used as substrate with similar results.

EXAMPLE 5

The conditions of Example 3 were followed except that the methyl ester of cyclopentane carboxylic acid, dissolved in methanol, was used as substrate with similar results.

EXAMPLE 6

The conditions of Example 3 were followed except that cyclopentane carboxylic acid, dissolved in methanol was used as substrate with similar results.

EXAMPLE 7

25- (Thien-3-yl) avermectin

A suspension of a slope culture of *S. avermitilis* NCIB 12121 was inoculated into 600 ml of a medium containing lactose (12.0 g), distillers solubles (8.0 g) and yeast extract (3.0 g) , contained in a 3 liter flask, and incubated at 28° C. for 3 days. The inoculum was used to inoculate 16 liters of a medium containing soluble starch (640 g), ammonium sulphate (32 g) , dipotassium hydrogen phosphate (16 g) , sodium chloride (16 g) , magnesium sulphate 7H$_2$O (16 g), calcium carbonate (32 g), soluble yeast extract (6.4 g), ferrous sulphate 7H$_2$O (0.016 g), zinc sulphate 7H$_2$O (0.016 g) and manganese chloride 4H$_2$O (0.016 g), contained in a 20 liter fermenter. The fermentation was incubated at 28° C., with agitation at 250 r.p.m. and aerated at 15 liters per minute. Thiophene-3-carboxylic acid sodium salt (1.6 g) was added after 24 hours and again after 48 and 72 hours incubation and the fermentation was continued for 120 hours. After this time the mycelium was removed by filtration and extracted with acetone: 1N-hydrochloric acid (100:1; 3×7 liters). The extract was concentrated to approximately 2 liters under reduced pressure and extracted with methylene chloride (2×5 liters). The methylene chloride extract was concentrated to dryness to give the crude product as a mobile oil which was dissolved in diethyl ether and added to a column of silica gel (1 kg). The column was eluted with diethyl ether collecting 200 ml fractions. Fractions 32–45 were combined and the solvent evaporated to yield partially purified material. The product was dissolved in a mixture of methanol and water (3:1) and chromatographed on a C18 Micro-Bondapack column (50 mm × 50 cm) in a Waters Prep 500 high pressure liquid chromatograph using the same solvent at a flow rate of 100 ml per minute. Fractions 27 to 36 containing the desired product were combined and rechromatographed on a C18 Zorbax ODS (Trademark, Dupont) column (21 mm × 25 cm) eluting with a mixture of methanol and water (3:1) at a flow rate of 9 ml per minute. The relevant fractions were combined and the solvent evaporated to yield the compound of formula (I) wherein R is H, $R^1$ is OH, $R^2$ is thien-3-yl, $R^3$ is $CH_3$ and $R^4$ is 4'-(alpha-L-oleandrosyl)-alpha-L-oleandrosyloxy as a white powder, m.p. 167° C. The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 953 (theoretical 953).

Electron impact mass spectrometry was performed using a VG Model 7070F mass spectrometer. The m/e values for the principal fragments were: 349, 331, 275, 265, 257, 247, 237, 219, 195, 145, 127, 113, 95 and 87.

EXAMPLE 8

A vegetative cell suspension of *S. avermitilis* NCIB 12121, held at −60° C. in 10% v/v aqueous (2 ml) glycerol was inoculated into 50 ml of medium containing lactose (1.0 g), distillers solubles (0.75 g) and yeast extract (0.25 g) contained in a 300 ml conical flask and incubated at 28° C. for 24 hours, with shaking. The inoculum was then added to 600 ml of the above medium contained in a 3 liter flask and the mixture was incubated at 28° C. for 24 hours with shaking. The product was used to inoculate 10 liters of the above medium contained in a 16 liter fermenter which was incubated at 28° C. for 24 hours at an agitation speed of 350 r.p.m. with aeration at 10 liters of air per minute. This fermentation (600 ml) was used to inoculate 16 liters of a medium containing partially hydrolysed starch (640 g) ammonium sulphate (32 g), dipotassium hydrogen phosphate (16 g), sodium chloride (16 g) magnesium sulphate $7H_2O$ (16 g), calcium carbonate (32 g), soluble yeast extract (6.4 g), ferrous sulphate $7H_2O$ (0,016 g), zinc sulphate $7H_2O$ (0.016 g), and manganese chloride $4H_2O$ (0.016 g), contained in a 20 liter fermenter. The fermentation was incubated at 28° C., with agitation at 350 r.p.m. and aerated at 15 liters per minute. Cyclobutane carboxylic acid sodium salt (1.6 g) was added after 24 hours and again after 48 and 72 hours incubation and the fermentation was continued for 120 hours. After this time the mycelium was removed by filtration and extracted with acetone (3 × 7 liters). The extract was concentrated to approximately 2 liters under reduced pressure and extracted with methylene chloride (2 × 5 liters). The methylene chloride was concentrated to dryness to give the crude product as a mobile oil. This was taken up in iso-octane (150 ml) and the solution extracted with a mixture of methanol (95 ml) and water (5 ml). Evaporation of the methanolic extract gave partially purified material which was separated into its individual components by high pressure liquid chromatography as follows: The residue was dissolved in a little methanol and chromatographed in a C18 Micro-Bondapack column (50 mm × 50 cm) in a Waters Prep 500 high pressure liquid chromatograph using a mixture of methanol/water (4:1) at a flow rate of 100 ml per minute. Fractions 1 to 4 were combined and used in Example 9, fractions 5 to 9 were combined and used in Example 10, fractions 10 to 19 were combined and used in Example 11 and fractions 20 to 35 were combined and used in Example 12.

EXAMPLE 9

25-Cyclobutyl-avermectin B2

($R^1$=OH, R and $R^3$=H)

The combined fractions 1 to 4 from Example 8 were evaporated to dryness and the residue was rechromatographed on a C18 Zorbax ODS (Trademark, Dupont) column (21 mm × 25 cm) eluting with a mixture of methanol and water (3:1) at a flow rate of 9 ml per minute. The relevant fractions were combined, the solvent evaporated and the product subjected to a final purification on a Silica Spherisorb 5 micron (Trademark, HPLC Technology) column (10.5 mm × 25 cm) eluting with a mixture of methylene chloride and methanol (98:2) at a flow rate of 4 ml per minute. The relevant fractions were combined and the solvent evaporated to yield the compound of formula (I) wherein R is H, $R^1$ is OH, $R^2$ is cyclobutyl, $R^3$ is H and $R^4$ is 4'-(alpha-L-oleandrosyl)-L-oleandrosyloxy, as a white powder, m.p. 110°–112° C. The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 911 (theoretical 911).

Electron impact mass spectrometry was performed using a VG Model 7070F mass spectrometer. The m/e values for the principal fragments were: 321, 303, 261, 257, 237, 219, 209, 191, 179, 167, 145, 127, 113, 111, 95 and 87.

EXAMPLE 10

25-Cyclobutyl-avermectin A2

($R^1$=OH, R=H, $R^3$=$CH_3$)

The combined fractions 5 to 9 from Example 8 were evaporated to dryness and the residue was rechromatographed twice on a C18 Zorbax ODS (Trademark, Dupont) column, (21 mm × 25 cm) eluting with a methanol and water mixture (77:23) at a flow rate of 9 ml per minute. Suitable fractions were combined and evaporated to yield the compound of formula (I) wherein R is H, $R^1$ is OH, $R^2$ is cyclobutyl, $R^3$ is $CH_3$ and $R^4$ is 4'-(alpha-L-oleandrosyl)-L-oleandrosyloxy, as a white powder, m.p. 135°–140° C.

The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 925 (theoretical 925).

Electron impact mass spectrometry was performed using a VG Model 7070F mass spectrometer. The m/e values for the principal fragments were: 596, 454, 321, 303, 275, 237, 219, 209, 191, 179, 167, 145, 127, 113, 111, 95 and 87.

EXAMPLE 11

25-Cyclobutyl-avermectin B1 (R and $R^1$ taken together=Double bond, $R^3$=H)

The combined fractions 10 to 19 from Example 8 were evaporated to dryness and the residue dissolved in methanol and chromatographed on a C18 Zorbax ODS (Trademark, Dupont) column, (21 mm×25 cm) eluting with a mixture of methanol and water (4:1) at a flow rate of 9 ml per minute. The relevant fractions were combined and the solvent evaporated to give a product which was rechromatographed on a Silica Zorbax SIL (Trademark, Dupont) column (21 mm×25 cm) eluting with a mixture of dichloromethane and methanol (98.5:1.5) at a flow rate of 9 ml per minute. The relevant fractions were combined and the solvent evaporated to yield the compound of formula (I) wherein R and $R^1$ taken together represent a double bond, $R^2$ is cyclobutyl, $R^3$ is H and $R^4$ is 4'-(alpha-L-oleandrosyl)-L-oleandrosyloxy, as a white powder, m.p. 135°–138° C.

The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 893 (theoretical 893).

Electron impact mass spectrometry was performed using a VG Model 7070F mass spectrometer. The m/e values for the principal fragments were: 303, 261, 257, 219, 191, 167, 145, 127, 113, 111, 95 and 87.

EXAMPLE 12

25-Cyclobutyl-avermectin A1

(R and $R^1$ taken together=Double bond, $R^3$=$CH_3$)

The combined fractions 20 to 35 from Example 8 were evaporated to dryness and the residue chromatographed on a C18 Zorbax ODS (Trademark, Dupont) column (21 mm×25 cm) at a flow rate of 9 ml per minute. The relevant fractions were combined, the solvent evaporated and the product was rechromatographed on a Silica Sperisorb 5 micron (Trademark, HPLC Technology) column (10.5 mm×25 cm) eluting with a mixture of dichloromethane and methanol (98.5:1.5) at a flow rate of 4 ml per minute. Combination of the relevant fractions followed by evaporation gave the compound of formula (I) wherein R and $R^1$ taken together represent a double bond, $R^2$ is cyclobutyl, $R^3$ is $CH_3$ and $R^4$ is 4'-(alpha-L-oleandrosyl)-L-oleandrosyloxy, as a white powder, m.p. 120°–124° C.

The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 907 (theoretical 907).

Electron impact mass spectrometry was performed using a VG Model 7070F mass spectrometer. The m/e values for the principal fragments were: 578, 303, 275, 257, 219, 191, 167, 145, 127, 113, 111, 95 and 87.

EXAMPLE 13

25-(Cyclohex-3-enyl) avermectin A2

The medium and conditions of Example 1 were followed except that 3-cyclohexenoic acid sodium salt was used as the substrate to yield the compound of formula I wherein R is H, $R^1$ is OH, $R^2$ is cyclohex-3-enyl, $R^3$ is $CH_3$ and $R^4$ is 4'-(alpha-L-oleandrosyl)-alpha-L-oleandrosyloxy, as a white powder, m.p. 131°–5° C.

The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 951 (theoretical 951).

Electron impact mass spectrometry was performed using a VG Model 7070F mass spectrometer. The m/e values for the principal fragments were: 624, 480, 329, 275, 245, 235, 217, 205, 193, 179, 145, 127, 113, 111, 95 and 87.

EXAMPLE 14

25-Cyclohexyl avermectin A2

The medium and conditions of Example 1 were followed except that cyclohexane carboxylic acid sodium salt was used as the substrate to yield the compound of formula I wherein R is H, $R^1$ is OH, $R^2$ is cyclohexyl, $R^3$ is $CH_3$ and $R^4$ is 4'-(alpha-L-oleandrosyl)-alpha-L-oleandrosyloxy, as a white powder, m.p. 112°–117° C.

The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 953 (theoretical 953).

Electron impact mass spectrometry was performed using a VG Model 7070F mass spectrometer. The m/e values for the principal fragments were: 624, 482, 349, 331, 275, 265, 247, 237, 219, 207, 195, 179, 145, 127, 113, 111, 95 and 87.

EXAMPLE 15

25-(1-Methylthioethyl) avermectin A2

The medium and conditions of Example 1 were followed except that 2-methylthiopropionic acid sodium salt was used as the substrate to yield the compound of formula I wherein R is H, $R^1$ is OH, $R^2$ is 1-methylthioethyl, $R^3$ is $CH_3$ and $R^4$ is 4'-(alpha-L-oleandrosyl)-L-oleandrosyloxy, as a white powder, m.p. 134°–138° C.

The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 945 (theoretical 945).

Electron impact mass spectrometry was performed using a VG Model 7070F mass spectrometer. The m/e values for the principal fragments were: 341, 323, 275, 263, 257, 239, 211, 187, 179, 145, 127, 113, 111, 95 and 87.

EXAMPLE 16

25-(2-Methylcyclopropyl) avermectin A2

The medium and conditions of Example 1 were followed except that 2-methylcyclopropane carboxylic acid sodium salt was used as the substrate to yield the compound of formula I wherein R is H, $R^1$ is OH, $R^2$ is 2-methylcyclopropyl, $R^3$ is $CH_3$ and $R^4$ is 4'-(alpha-L- oleandrosyl)-L-oleandrosyloxy, as a white powder, m.p. 147°–150° C.

The structure of the product was confirmed by mass spectrometry as follows:

Fast atom bombardment mass spectrometry was performed on a VG Model 7070E mass spectrometer using a sample matrix of triethylene glycol with solid sodium chloride. $(M+Na)^+$ observed at m/e 925 (theoretical 925).

Electron impact mass spectrometry was performed using a VG Model 7070F mass spectrometer. The m/e values for the principal fragments were: 596, 454, 303, 275, 237, 219, 209, 191, 179, 167, 145, 127, 113, 111, 95 and 87.

EXAMPLE 17

The procedure of Example 1 was followed but using the sodium salt of the following carboxylic acids as substrate instead of cyclopentane carboxylic acid to yield the appropriate 25-substituted avermectins of formula (I) wherein R is H, $R^1$ is OH, or R and $R^1$ taken together represent a double bond, $R^3$ is H or OH and $R^4$ is 4'-(alpha-L-oleandrosyl)-alpha-L-oleandrosyloxy:

2-methylvaleric acid
2,3-dimethylbutyric acid
2-methylhexanoic acid
2-methylpent-4-enoic acid
2-cyclopropyl propionic acid
cycloheptane carboxylic acid
4,4-difluorocyclohexane carboxylic acid
4-methylenecyclohexane carboxylic acid
3-methylcyclohexane carboxylic acid
cyclopentene-1-carboxylic acid
1-cyclohexene carboxylic acid
tetrahydropyran-4-carboxylic acid and
3-furoic acid
and 2-chloro-thiophene-4-carboxylic acid.

EXAMPLE 18

Repetition of the procedure of Example 17 but using the carboxylic acids (as their sodium salts) enumerated below, the appropriate 25-substituted avermectins characterized in Table I were obtained:

cyclohexane carboxylic acid
cyclohex-3-ene carboxylic acid
cyclopentane carboxylic acid
2-methylpent-3-enoic acid
2-methylpropionic acid
thiophene-3-carboxylic acid
exomethylenecyclohexane carboxylic acid
furan-3-carboxylic acid
2-methylvaleric acid
thiophene-2-carboxylic acid
tetrahydropyran-4-carboxylic acid
2-methyl-4-methoxybutyric acid
2-methylpent-3-ynoic acid
cyclopent-3-ene carboxylic acid
3,4-dihydropyran-2-carboxylic acid.

TABLE 1

| | Physical and Spectroscopic Data for Novel C-25 Avermectins | | | | |
|---|---|---|---|---|---|
| Substituent ($R^2$) | Subclass | m.p. °C. | Theoretical Mol. Wt. | $(M + Na)^+$ From FAB Mass Spec. | m/e for Principle Fragments in the EI Mass. Spec. |
| Cyclohexyl | A1 | 110–115 | 912 | 935 | 606, 331, 275, 257, 247, 218, 195, 145, 127, 113, 95 and 87. |
| | B1 | 116–9 | 898 | 921 | 592, 331, 257, 247, 219, 195, 145, 127, 113, 95 and 87. |
| | B2 | 146–8 | 916 | 939 | 610, 482, 349, 331, 275, 265, 257, 179, 145, 127, 113, 95 and 87. |
| | $H_2B1^*$ | 150 (dec) | 900 | 923 | 594, 333, 249, 221, 145, 127, 113, 95 and 87. |
| 3-Cyclohexenyl | B1 | 122–129 | 896 | 919 | 590, 329, 257, 245, 217, 193, 145, 127, 113, 95 and 87. |
| Cyclopentyl | B1 | 158–162 | 884 | 907 | 578, 468, 317, 257, 233, 205, 145, 127, 113, 95 and 87. |
| | B2 | 158–164 | 902 | 925 | 596, 468, 335, 317, 257, 251, 233, 179, 145, 127, 113, 95 and 87. |
| | $H_2B1^*$ | 145–147 | 886 | 909 | 580, 319, 257, 207, 145, 127, 113, 95 and 87. |
| 1-Methylbut-3-enyl | A2 | 149–151 | 916 | 939 | 610, 335, 317, 275, 251, 233, 223, 205, 179, 145, 127, 113, 95 and 87. |
| | B1 | 141–144 | 884 | 907 | 596, 578, 317, 261, 257, 233, 205, 145, 127, 113, 95 and 87. |
| 1-Methylthioethyl | B1 | 144–147 | 890 | 913 | 584, 323, 261, 257, 239, 211, 187, 145, 127, 113, 95 and 87. |
| 3-Thienyl | B1 | 155–165 | 898 | 921 | 610, 592, 574, 482, 331, 261, 257, 247, 219, 195, 145, 127, 113, 95 and 87. |
| | B2 | 175–180 | 916 | 939 | 610, 331, 257, 249, 234, 219, 179, 145, 127, 113, 95 and 87. |
| Exomethylenecyclohexyl | B1 | 161–165 | 910 | 933 | 604, 343, 261, 259, 231, 207, 145, 127, 113, 95 and 87. |
| 3-Furanyl | A2 | 148–153 | 914 | 937 | 333, 315, 275, 257, 249, 231, 221, 203, 179, 145, |

TABLE 1-continued

Physical and Spectroscopic Data for Novel C-25 Avermectins

| Substituent (R²) | Sub-class | m.p. °C. | Theoretical Mol. Wt. | (M + Na)⁺ From FAB Mass Spec. | m/e for Principle Fragments in the EI Mass. Spec. |
|---|---|---|---|---|---|
| | B1 | 145–150 | 882 | 905 | 127, 113, 95 and 87. 576, 315, 261, 257, 231, 203, 179, 145, 127, 113, 95 and 87. |
| 1-Methylbutyl | A1 | — | 900 | 923 | 594, 470, 319, 275, 257, 207, 183, 145, 127, 113, 95 and 87. |
| | B1 | 148–150 | 886 | 909 | 580, 337, 319, 261, 257, 253, 225, 207, 183, 145, 127, 113, 111, 95 and 87. |
| 2-Thienyl | B1 | 152–154 | 898 | 921 | 592, 331, 257, 247, 219, 195, 145, 127, 113, 95 and 87. |
| 4-Tetrahydropyranyl | A1 | 175–176 | 914 | 937 | 608, 333, 275, 249, 221, 197, 145, 127, 113, 95, and 87. |
| | A2 | 220 (dec) | 932 | 955 | 351, 333, 275, 267, 249, 239, 221, 197, 145, 127, 113, 95 and 87. |
| | B1 | 177–183 | 900 | 923 | 594, 333, 249, 197, 145, 127, 113, 95 and 87. |
| | B2 | 173–178 | 918 | 941 | 612, 351, 333, 267, 261, 249, 239, 221, 207, 197, 145, 127, 113, 95 and 87. |
| | H₂B1* | 160–163 | 902 | 925 | 486, 335, 269, 261, 257, 251, 223, 199, 145, 127, 113, 95 and 87. |
| 1-Methyl-3-methoxypropyl | B1 | 143–150 | 902 | 925 | 596, 335, 257, 251, 223, 199, 145, 127, 113, 95 and 87. |
| 1-Methylbut-3-ynyl | B1 | 95–100 | 882 | 905 | 576, 466, 315, 261, 257, 231, 203, 179, 145, 127, 113, 95 and 87. |
| | B2 | 107–110 | 900 | 923 | 594, 466, 333, 315, 261, 257, 249, 231, 221, 203, 179, 145, 127, 113, 95 and 87. |
| 3-Cyclopentenyl | B1 | 150–152 | 882 | 905 | 576, 315, 261, 257, 248, 239, 231, 211, 203, 179, 145, 127, 113, 95 and 87. |
| 3,4-Dihydro-pyran-2-yl | A1 | 130–135 | 912 | 935 | 331, 275, 257, 247, 219, 195, 145, 127, 113, 95 and 87. |

*H₂B1 = dihydro B1 derivative. Prepared from corresponding B1 derivative by the procedure of Example 20.

EXAMPLE 19

25-Cyclobutyl-22,23-dihydro-avermectin B1

The product of Example 11 in benzene is hydrogenated in the presence of tris(triphenylphosphine)rhodium (I) chloride according to the procedure of EP-A-0001689 to yield the corresponding compound of formula (I) wherein each of R and R¹ is H. The product of Example 12 is similarly converted to the corresponding dihydro derivative.

EXAMPLE 20

25-Cyclohexyl-22,23-dihydro-avermectin B1

Dry benzene (200 ml) was purged first with a stream of nitrogen, then hydrogen. Tris(triphenylphosphine)rhodium (I) chloride (Wilkinson's catalyst) (665 mg) was then added. The passage of hydrogen was continued until the solution was yellow, and then for a further 10 minutes. 25-Cyclohexyl-avermectin B1 (2.010 g) was then added under a nitrogen blanket, and hydrogen bubbled through the solution for 24 hours. The solution was then evaporated to dryness. The residue was dissolved in methanol (50 ml) and evaporated; this was repeated. The residue was extracted with two portions of a 3:1 ether:hexane mixture (2×100 ml), and filtered. The combined filtrates were evaporated to dryness and chromatographed over silica gel (250 g of 230–900 mesh), eluting with an ether:methanol mixture (9:1). The relevant fractions were combined and evaporated to dryness to give crude product (2.25 g). This was purified using preparative HPLC, in three batches of 750 mg each, on a 42 mm×30 cm Dynamax column, eluting initially with methanol:water (85:15), graduating to methanol:water (83:17) over 15 minutes, at a flow rate of 95 ml/min. Appropriate fractions were pooled and evaporated to give the title compound (1.43 g; 81%) as a white powder, m.p. 150° C. (dec.). (See Table 1 for additional characterizing data.)

EXAMPLE 21

13-Deoxy-25-cyclopentyl-avermectin A2-aglycone

The product of Example 1 is treated with dilute sulphuric acid at room temperature and the resulting aglycone product is isolated and reacted with t-butyldimethylsilylchloride in dimethylformamide to provide the 23-O-t-butyldimethylsilyl aglycone derivative. This is dissolved in methylene chloride containing 4-dimethylaminopyridine and diisopropylethylamine, cooled in ice and treated dropwise with 4-nitrobenzenesulphonylchloride to yield the 13-chloro-13-deoxy product. This is finally dehalogenated by reaction with tributyltinhydride and deprotected with methanol containing a trace of paratoluene sulphonic acid following the procedures described in EP-A-0002615 to provide the compound of the formula I wherein each of R, $R^1$ and $R^4$ is H, $R^3$ is OH, and $R^2$ is cyclopentyl. In like manner, the compounds of Examples 7–10 and 13–20 are converted to the corresponding 13-deoxy derivatives.

EXAMPLE 22

Drench Formulation

The product of any one of the preceding Examples was dissolved in polyethylene glycol (average molecular weight 300) to give a solution containing 400 micrograms/ml for use as a drench formulation.

EXAMPLE 23

Anthelmintic Activity

Anthelmintic activity was evaluated against *Caenorhabditis elegans* using the in vitro screening test described by K. G. Simpkin and G. L. Coles in Parisitology, 1979, 79, 19. The products of Examples 1, 7 and 9–16 all killed 100% of the worms at a well concentration of 0.1 micrograms per ml.

EXAMPLE 24

Insecticidal Activity

Activity against adult house fly *Musca domestica* is demonstrated using a standard test procedure in which flies are anaesthetised under carbon dioxide and 0.1 microliters of acetone containing the test compound is deposited on the thorax of female flies. The product of Examples 1, 7 and 9–16 all killed 100% of the treated flies at a dose of 0.01 micrograms per fly.

We claim:

1. A process for producing a compound having the formula

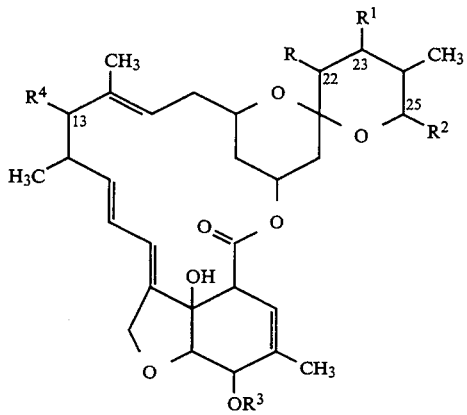

wherein R when taken individually is H; $R^1$ when taken individually is OH; R and $R^1$ when taken together represent a double bond;

$R^2$ is an alpha-branched $C_5-C_8$ alkyl, $C_3-C_8$ alkenyl, $C_4-C_8$ alkynyl, $C_3-C_8$ alkoxyalkyl or $C_3-C_8$ alkylthioalkyl group; a $C_5-C_8$ cycloalkylalkyl group wherein the alkyl group is an alpha-branched $C_2-C_5$ alkyl group; a $C_3-C_8$ cycloalkyl or $C_5-C_8$ cycloalkenyl group, either of which may be substituted by methylene or one or more $C_1-C_4$ alkyl groups or halo atoms; or a 3 to 6 membered oxygen or sulphur containing heterocyclic ring which may be saturated, or fully or partially and which may be substituted by one or more $C_1-C_4$ alkyl groups or halo atoms;

$R^3$ is hydrogen or methyl; and $R^4$ is a 4'-(alpha-L-oleandrosyl)-alpha-L-oleandrosyloxy group of the formula:

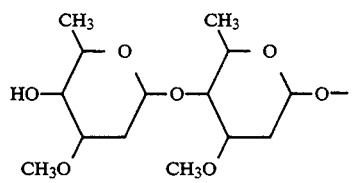

which comprises fermenting an avermectin producing strain of the organism *Streptomyces avermitilis* in a medium comprising assimilable sources of carbon, nitrogen and trace elements and in the presence of a carboxylic acid of the formula $R^2CO_2H$, or a salt, ester or amide thereof or oxidative precursor therefor, wherein $R^2$ is as defined above.

2. A process according to claim 1 wherein the organism is *Streptomyces avermitilis* NCIB 12121.

3. A process according to claim 1 wherein the organism is *Streptomyces avermitilis* NCIB 12121.

4. A process according to claim 1 wherein $R^2$ is cyclohexyl.

* * * * *

UNITED STATES PATENT AND TRADEMARK OFFICE
CERTIFICATE OF CORRECTION

PATENT NO. : 5,451,511

DATED : September 19, 1995

INVENTOR(S) : Stephen P. Gibson et al.

It is certified that error appears in the above-identified patent and that said Letters Patent is hereby corrected as shown below:

U.S. Patent Documents, page 2 - "Chabla et al." should read -- Chabala et al. --.

Column 1, line 27 - insert -- in -- before "an".

Column 2, line 19 - delete "when taken" after "H;".

Column 2, line 63 - "$C_1C_4$" should read -- $C_1-C_4$ --.

Column 6, line 37 - "0,001" should read -- 0.001 --.

Column 9, line 49 - "(0,016 g)" should read -- (0.016 g) --.

Column 12, line 14 - insert -- 347 -- after "480".

Column 14, line 6 - delete "and" after "acid".

Column 14, Table I heading - "Substituent ($R^2$)" should read -- 25 Substituent ($R^2$) --.

UNITED STATES PATENT AND TRADEMARK OFFICE
CERTIFICATE OF CORRECTION

PATENT NO. : 5,451,511

DATED : September 19, 1995

INVENTOR(S) : Stephen P. Gibson et al.

It is certified that error appears in the above-identified patent and that said Letters Patent is hereby corrected as shown below:

Column 18, lines 55, 56 - Claim 3 should read -- A process according claim 1 wherein $R^2$ is cyclohexyl. --.

Column 18, lines 56, 57 - Claim 4 should read -- A process according claim 3 wherein the organism is *Streptomyces avermitilis* NCIB 12121. --.

Signed and Sealed this

Twenty-first Day of July, 1998

Attest:

BRUCE LEHMAN

*Attesting Officer*   *Commissioner of Patents and Trademarks*